(12) United States Patent
Schell et al.

(10) Patent No.: US 10,288,480 B2
(45) Date of Patent: May 14, 2019

(54) OPTICAL FILTER, OPTICAL DEVICE AND METHOD FOR DETERMINING A PROPERTY OF A SUBSTANCE BY USING AN OPTICAL FILTER

(71) Applicant: Fraunhofer-Gesellschaft zur Förderung der angewandten Forschung e.V., Munich (DE)

(72) Inventors: Martin Schell, Berlin (DE); Magnus Happach, Berlin (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 0 days.

(21) Appl. No.: 15/578,903

(22) PCT Filed: Jun. 1, 2016

(86) PCT No.: PCT/EP2016/062377
§ 371 (c)(1),
(2) Date: Dec. 1, 2017

(87) PCT Pub. No.: WO2016/193304
PCT Pub. Date: Dec. 8, 2016

(65) Prior Publication Data
US 2018/0172513 A1 Jun. 21, 2018

(30) Foreign Application Priority Data

Jun. 2, 2015 (DE) .................. 10 2015 210 215

(51) Int. Cl.
*G01N 21/00* (2006.01)
*G01J 3/26* (2006.01)
(Continued)

(52) U.S. Cl.
CPC ............... *G01J 3/26* (2013.01); *G01J 3/0205* (2013.01); *G01J 3/0208* (2013.01);
(Continued)

(58) Field of Classification Search
CPC ... G02F 1/025; G02F 2001/213; G02B 5/284; G01J 3/0205; G01J 3/0256; G01J 3/26
(Continued)

(56) References Cited

U.S. PATENT DOCUMENTS 5,091,983 A    2/1992  Lukosz
5,859,717 A *  1/1999  Scobey .............. G02B 6/29367
                                                    385/24
(Continued)

FOREIGN PATENT DOCUMENTS

DE    60311048 T2    5/2007

OTHER PUBLICATIONS

Hulme et al.; "Fully integrated hybrid silicon free-space beam steering source with 32 channel phased array"; Smart Photonic and Optoelectronic Integrated Circuits XVI; 2014; vol. 8989 898907-1; SPIE.
(Continued)

*Primary Examiner* — Hoa Q Pham
(74) *Attorney, Agent, or Firm* — The Webb Law Firm

(57) ABSTRACT

An optical filter for an optical data transmission system, including a substrate; a first and a second reflective structure which are spaced apart from each other such that they form a Fabry-Perot cavity, and at least one optical waveguide formed on or in the substrate, via which light can be coupled into the Fabry-Perot cavity and/or out of the Fabry-Perot cavity. The Fabry-Perot cavity formed by the first and the second reflective structure at least partly is a free-beam cavity, and the waveguide is an integrated waveguide which is formed by one or more layers arranged on the substrate,
(Continued)

and the first and the second reflective structure are at least partly arranged in a cutout of the substrate or adjoin the cutout.

17 Claims, 2 Drawing Sheets

(51) Int. Cl.
*G01J 3/02* (2006.01)
*G01J 3/45* (2006.01)
*G01N 21/27* (2006.01)

(52) U.S. Cl.
CPC .......... *G01J 3/0229* (2013.01); *G01J 3/0256* (2013.01); *G01J 3/45* (2013.01); *G01N 21/27* (2013.01)

(58) Field of Classification Search
USPC ....... 356/519, 480, 477, 432–440, 244, 246; 385/50, 51, 14, 129; 359/579, 578
See application file for complete search history.

(56) References Cited

U.S. PATENT DOCUMENTS

| | | | | |
|---|---|---|---|---|
| 6,445,838 | B1 | 9/2002 | Caracci et al. | |
| 6,608,685 | B2 | 8/2003 | Wood et al. | |
| 6,618,524 | B2 | 9/2003 | Lee et al. | |
| 6,980,362 | B2* | 12/2005 | Lewis | G02B 5/284 359/580 |
| 7,428,351 | B2* | 9/2008 | Jenkins | G02B 6/122 385/129 |
| 7,634,163 | B2* | 12/2009 | Moy | G02B 6/29395 385/33 |
| 2004/0067023 | A1* | 4/2004 | Hanashima | G02B 6/12007 385/43 |
| 2004/0086228 | A1 | 5/2004 | Rumpf et al. | |
| 2005/0053101 | A1* | 3/2005 | Liu | H01S 3/0675 372/6 |
| 2009/0153844 | A1* | 6/2009 | Peter | G01N 21/05 356/128 |
| 2009/0180729 | A1* | 7/2009 | Rasras | G02B 6/12007 385/11 |
| 2010/0238454 | A1* | 9/2010 | Pruessner | G01G 3/165 356/479 |
| 2014/0362442 | A1* | 12/2014 | Chen | G02B 26/001 359/579 |

OTHER PUBLICATIONS

Jestel; "Integrated Optical Michelson-Interfermoter in Glass; Micro-Optics"; 1988; pp. 31-34; vol. 1014; SPIE.
Kinoshita et al; "Development of Compatible Air-Gap Etalons Used with both Terahertz Wave and Near-Infrared Light"; 2012; IEEE.
Pruessner et al.; "Integrated waveguide Fabry-Perot microcavities with silicon/air Bragg mirrors"; Opitics Letters; Mar. 1, 2007; pp. 533-535; vol. 32, No. 5; Optical Society of America.
Pruessner et al.; "Thermo-optic tuning and switching in SOI waveguide Fabry-Perot microcavities"; Optics Express; Jun. 11, 2007; pp. 7557-7585; vol. 15, No. 12; Optical Society of America.
Ren et al.; "On-Chip Collimated Planar 'Free Space' Gaussian Beams utilising Optical Lenses on a Silicon on Insulator Chip"; 2013; IEEE.
Ren et al.; "Gaussian Beams on a Silicon-on-Insulator Chip Using Integrated Optical Lenses"; IEEE Photonics Technology Letters; Jul. 15, 2014; pp. 1438-1441; vol. 26, No. 14; IEEE.
Stone et al.; "Narrow-Band FiEnd Etalon Filters Using Expanded-Core Fibers"; Journal of Lightwave Technology; Dec. 1992; pp. 1851-1854; vol. 10, No. 12; IEEE.
Vanderleeden; "Resonant cavities with mirrors made from graded-index rods"; Journal of Applied Physics; Jan. 1974; vol. 45, No. 1, pp. 201-208; American Institute of Physics.
Wang et al.; "A GRIN medium coupler and its application in light beam spot conversion"; Information Optics and Optical Data Storage II; 2012; vol. 8559 85590Q; SPIE.
Wei et al.; "Temperature-insensitive miniaturized fiber inline Fabry-Perot interferometer for highly sensitive refractive index measurement"; Optics Express; Apr. 14, 2008; pp. 5764-5769; vol. 16, No. 8; Optical Society of America.
Wieduwilt et al.; "Reflectivity enhanced refractive index sensor based on a fiber-integrated Fabry-Perot microresonator"; Optics Express; Oct. 20, 2014; pp. 25333-25346; vol. 22, No. 21; Optical Society of America.
Yang et al.; "Performance of Extrinsic Fabry-Perot Interferometer Based on Graded-Index Lenses for a Fabry-Perot cavity with Surface Errors"; Journal of Russian Laser Research; Jul. 2013; pp. 402-407; vol. 34, No. 4; Springer Science + Business Media, New York.
Zickar et al.; "MEMS compatible micro-GRIN lenses for fiber to chip coupling of light"; Optics Express; Apr. 2006; pp. 4237-4249; vol. 14, No. 10; Optical Society of America.

* cited by examiner

OPTICAL FILTER, OPTICAL DEVICE AND METHOD FOR DETERMINING A PROPERTY OF A SUBSTANCE BY USING AN OPTICAL FILTER

CROSS-REFERENCE TO RELATED APPLICATIONS

This application is the United States national phase of International Application No. PCT/EP2016/062377 filed Jun. 1, 2016, and claims priority to German Patent Application No. 10 2015 210 215.7 filed Jun. 2, 2015, the disclosures of which are hereby incorporated in their entirety by reference.

BACKGROUND OF THE INVENTION

Field of the Invention

This invention relates to an optical filter, in particular for an optical data transmission system, an optical device, and a method for determining a property of a substance by using an optical filter.

Description of Related Art

Optical filters constructed in the manner of a Fabry-Perot resonator (Fabry-Perot cavity) are known from the prior art. Such filters are used for example for the wavelength stabilization of a laser. In particular, by using such filters a feedback signal is used for controlling a laser of an optical data transmission system, for example of a DWDM—Dense Wavelength Division Multiplexing—transmission network, or in coherent optical systems.

A possibility for realizing a Fabry-Perot resonator is disclosed in U.S. Pat. No. 6,608,685. Furthermore, the article "Integrated waveguide Fabry-Perot microcavities with silicon/air Bragg mirrors", M. W. Pruessner et al., OPTICS LETTERS, Vol. 32, No. 5, p. 533 describes a chip-integrated Fabry-Perot resonator. Such integrated Fabry-Perot resonators, however, have the disadvantage that the resonator exhibits dispersion and is temperature-sensitive, so that the properties of a filter realized with such Fabry-Perot resonator are wavelength- and temperature-dependent.

SUMMARY OF THE INVENTION

A problem underlying the invention consists in realizing an optical filter as compact as possible with the lowest possible dispersion and temperature dependence.

This problem is solved by the filter with features as described herein.

Accordingly, there is provided a filter for an optical data transmission system, comprising
  a substrate;
  a first and a second reflective structure, which are spaced apart from each other such that they form a Fabry-Perot cavity (etalon or resonator), at least one optical waveguide formed on or in the substrate, via which light can be coupled into the Fabry-Perot cavity and/or out of the Fabry-Perot cavity, wherein
  the Fabry-Perot cavity formed by the first and the second reflective structure at least partly is a free-beam cavity, and the waveguide is an integrated waveguide which is formed by one or more layers arranged on the substrate, wherein the first and the second reflective structure are at least partly arranged in a cutout of the substrate or adjoin the cutout.

The fact that the Fabry-Perot cavity is formed as "free-beam cavity" in particular means that the light coupled into the cavity undergoes no guidance there at least in a direction vertical to its propagation direction. For example, no lateral guidance of the light is effected in the cavity, i.e. no guidance in a direction vertical to the propagation of light and parallel to the substrate. It is of course also conceivable that the light is not guided at all in the cavity. For example, the cavity merely is filled with air, in order to realize the lowest possible dispersion and/or temperature dependence of the filter properties. It is also conceivable, however, that the cavity is at least partly filled with a substance (e.g. a solid or a gas different from air), in order to be able to adapt the dispersion and/or the temperature dependence of the filter properties in the desired way. The substance, however, at least effects no lateral guidance of the light coupled into the cavity.

The at least one integrated optical waveguide provides for coupling light into and/or out of the Fabry-Perot cavity on the substrate (on the waveguide platform), whereby coupling losses can be reduced or even substantially be avoided. In one embodiment of the invention at least two optical waveguides are provided, wherein via the one waveguide light can be coupled into the Fabry-Perot cavity and via the other waveguide light can be coupled out of the cavity.

The substrate includes a cutout, wherein the first and the second reflective structure are arranged in the cutout or adjoin the cutout.

The free spectral range of the Fabry-Perot cavity is defined by the distance between the reflective structures, so that the length of the cutout and/or the position of the reflective structures in the cutout in particular is chosen in dependence on the desired free spectral range. Furthermore, the first and/or the second reflective structure can include a reflection coating (i.e. a reflection-increasing coating), in order to adjust the finesse of the Fabry-Perot cavity. In particular, the coating is a highly reflective coating. The coatings of the first and the second reflective structure in particular are different; for example, the second reflective structure, via which light is coupled out of the Fabry-Perot cavity, has a lower reflectivity than the first reflective structure, via which light is coupled into the Fabry-Perot cavity. The reflective structures (and possibly their coatings) in particular are of the partially reflective type, in order to provide for coupling light into and out of the cavity.

The substrate for example is formed of silicon, silicon dioxide or an organic material, wherein a "substrate" also is understood to be a substrate provided with material layers. For example, the cutout extends through at least one material layer into the actual substrate.

It is also conceivable that the first and/or the second reflective structure are formed by a side wall defining the cutout. For example, the side wall is formed by the substrate, i.e. the side wall forms at least one reflective facet which forms the first and/or the second reflective structure of the cavity. The light in particular is guided to the cavity via a taper (see below), in order to reduce the divergence of the light coupled into the cavity (and parallelize the light as far as possible).

It is also conceivable, however, that the first and/or the second reflective structure each are formed by a surface of a lens, wherein the lenses are arranged e.g. in the cutout. In particular, both the first and the second reflective structure each are formed by a surface of a lens. For example, the lens (or the lenses) is a GRIN lens (gradient index lens). The lens in particular is formed such that it parallelizes incoming light. The lens, if it is a GRIN lens, for example has a pitch of $L/\lambda = 0.25$ (L: thickness of the lens in beam direction, $\lambda$: wavelength of the incident light). It is also conceivable that only one of the two reflective structures is formed as lens and the other reflective structure is formed by a side wall of the substrate defining the cutout.

According to another aspect of the invention the first reflective structure is formed by a surface of a first lens portion of a lens body and the second reflective structure is formed by a surface of a second lens portion of the lens body. For example, the first and/or the second lens portion each form a GRIN lens. It is also possible in particular that the lens body is formed in one piece; e.g. of glass or a plastic material. The lens portions in particular are disposed on sides of a recess present in the lens body which face away from each other.

The lens body can be arranged in the above-mentioned cutout of the substrate, wherein the surfaces of the first and the second lens portion adjoining the recess in the lens body form the first and the second reflective structure of the filter according to the invention. The use of a common lens body for forming the first and the second lens can have the advantage that the distance of the lenses, i.e. of the reflective structures, from each other is fixed and does not change when the lenses are fixed on the substrate.

The invention, however, also comprises the variant that the lens body is not arranged in the cutout of the substrate, but for example on a surface of the substrate and e.g. via suitable coupling structures is connected with the optical waveguide (or the optical waveguides) of the filter. In this variant, the surfaces of the first and the second lens portion adjoining the recess of the lens body form the first and the second reflective structure of the Fabry-Perot cavity.

The filter according to the invention in addition can include a taper (i.e. a mode converter), via which light can be coupled into the Fabry-Perot cavity. Via the taper, the optical waveguide for example is coupled with the above-mentioned lens or the side wall. The taper in particular is a waveguide structure (e.g. integrally formed with the optical waveguide) which tapers towards the Fabry-Perot cavity (e.g. towards the lens). Depending on the design of the Fabry-Perot cavity and/or of the waveguide, the taper also can flare towards the Fabry-Perot cavity. It also is possible that a further taper is present, via which light can be coupled out of the Fabry-Perot cavity.

It is also conceivable that the filter according to the invention includes a heating device for tempering at least a portion of the Fabry-Perot cavity. The heating device in particular serves to temper a substance with which at least a portion of the Fabry-Perot cavity is filled or which is arranged in the Fabry-Perot cavity. In particular, by varying the temperature of the filter, i.e. the temperature in the region of the Fabry-Perot cavity or of the substance present in the Fabry-Perot cavity, properties of the filter (in particular the location of the transmission maxima) can be varied. The heating device for example includes at least one electric electrode to which an electric current can be applied.

It is also conceivable that only a partial region of the Fabry-Perot cavity is filled with a (in particular dispersive) substance or such substance is arranged in a partial region of the Fabry-Perot cavity, wherein in particular only this partial region is tempered. The filled and tempered partial region of the Fabry-Perot cavity in particular forms a phase shifter. The substance for example is a polymer, a UV-curing material (e.g. liquid crystals) or a magneto-optical material which e.g. changes the polarization of the light. It is also conceivable that the substance is a solid piece of material, e.g. a glass element (such as a glass block). In addition, said substance also can be arranged in the cavity when no heating device is present.

In a second aspect, the invention relates to an optical device, in particular an optical filter, in particular as described above, comprising
  a substrate;
  at least one optical waveguide formed (i.e. integrated) on or in the substrate,
  wherein the substrate includes a cutout,
  and wherein light can be coupled into the cutout and/or out of the cutout via the optical waveguide, and the cutout is formed such that the light can propagate in the cutout at least partly as free beam,
  wherein in the cutout at least one light-influencing device is arranged such that light can be coupled into the light-influencing device as free beam and/or light can be coupled out of the light-influencing device as free beam, wherein
  the waveguide is an integrated waveguide which is formed by one or more layers arranged on the substrate, and wherein the first and the second reflective structure are at least partly arranged in a cutout of the substrate or adjoin the cutout.

For example, the light-influencing device 5 is an optical isolator, an optical circulator, a phase shifter and/or an optical amplifier. It is also conceivable that in the cutout a Fabry-Perot cavity is formed or the cutout forms a Fabry-Perot cavity. The formation of the cavity in particular is effected by arranging reflective structures in the cavity or by the fact that side walls (oriented vertically to the light propagation) of the cutout form reflective structures, as described above in connection with the first aspect of the invention. In particular, the reflective structures include a corresponding reflection coating.

It is also possible, however, that the cutout is not formed as Fabry-Perot resonator, but merely forms a free-beam region. In this exemplary embodiment it is even possible that the side walls of the cutout, via which the light is coupled into and out of the cutout, are provided with an anti-reflection coating.

The invention also relates to a method for determining a property of a substance by using an optical filter which includes:
  a substrate;
  a first and a second reflective structure, which are spaced apart from each other such that they form a Fabry-Perot cavity at least partly formed as free-beam cavity; and
  at least one optical waveguide formed on or in the substrate, via which light can be coupled into the Fabry-Perot cavity and/or out of the Fabry-Perot cavity,
the method comprising the following steps:
  filling of the Fabry-Perot cavity of the filter with the substance;
  coupling of light into the Fabry-Perot cavity;
  receiving of light coupled out of the Fabry-Perot cavity;
  determining at least one property of the substance with reference to a spectrum of the light coupled out.

In particular, the method according to the invention provides for a determination of the index of refraction of the substance present in the cutout of the filter. The substance to be examined for example is a liquid, e.g. a body fluid (such as blood).

It is also conceivable that the substance is a gas; e.g. a gas with particles or an aerosol. Thus, the optical filter described above also is usable as detector (in particular as gas and/or fluid detector); e.g. as smoke detector or in the manner of a gas interferometer for the detection of gas (e.g. methane gas). It also is possible that the cavity is pre-filled with a gas and the filter is used as pressure sensor. It is also possible, however, that the substance to be examined is a solid piece of material.

BRIEF DESCRIPTION OF THE DRAWINGS

The invention will be explained in detail below by means of exemplary embodiments with reference to the Figures, in which.

DESCRIPTION OF THE INVENTION

Figure 1:
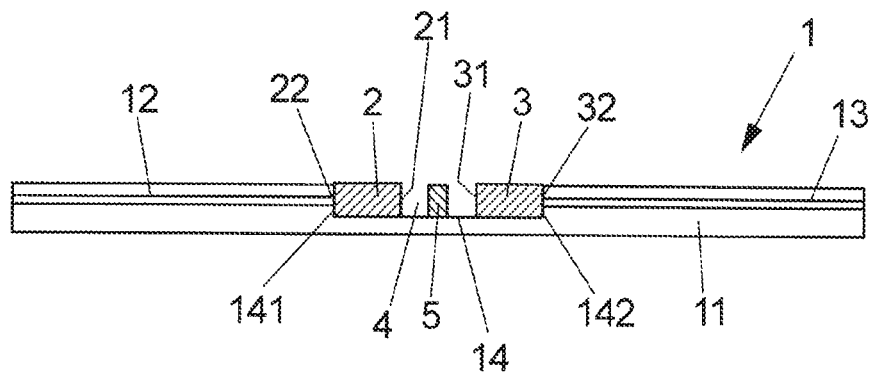
FIG. 1 shows a sectional view of a filter according to an exemplary embodiment of the invention.

The optical filter 1 shown in FIG. 1 comprises a substrate 11 (such as a waveguide platform) as well as a first optical waveguide 12 and a second optical waveguide 13. The optical waveguides 12, 13 are integrated waveguides which each are formed by one or more layers arranged on the substrate 11. For the lateral guidance of the light the waveguides 12, 13 in a manner known per se for example include a strip or rib structure. Above a waveguide core of the waveguides 12, 13 a cladding layer can be disposed.

The filter 1 according to the invention furthermore includes a first reflective structure in the form of a surface 21 of a lens (GRIN lens 2) arranged in a cutout 14 of the substrate 11. In the cutout 14 there is also disposed a second GRIN lens 3 which with a surface 31 facing the surface 21 of the first lens 2 forms a second reflective structure. The cutout 4 in particular is formed as trench in the substrate 11, which e.g. has a U-shaped cross-section (as seen along the light propagation).

The GRIN lenses 2, 3 each e.g. have an at least approximately cylindrical shape or a cuboid shape. The surfaces (end faces) 21, 31 of the lenses 2, 3 correspondingly extend at least approximately parallel to each other and are arranged in the cutout 14 with a distance to each other, so that a Fabry-Perot cavity 4 is formed between the surfaces 21, 31.

Via the first waveguide (input waveguide) 12 and the first GRIN lens (input lens) 2 light can be coupled into the cavity 4. The cavity 4 is formed as free-beam cavity, so that the light coupled in via the first waveguide 12 propagates as free beam in the cavity 4 up to the second lens 3. Between the surfaces 21, 31 of the lenses 2, 3 the light is reflected back and forth, whereby the known filter properties of a Fabry-Perot resonator are obtained. Via the second lens (output lens) 3 and the second waveguide (output waveguide) 13 light is coupled out of the cavity 4. The light coupled out for example is used for the wavelength stabilization of a laser, as already mentioned above.

The lenses 2, 3 in particular are cohesively connected with the substrate 11; for example, an adhesive each is present between the sides 22, 32 of the lenses 2, 3 facing away from (and extending parallel to) the surfaces 21, 31 and the side walls 141, 142 of the cutout 14. The adhesive in addition can have optically damping properties, so that internal "sub-cavities" between the surfaces 21, 31 and the sides 22, 32 of the lenses 2, 3 are suppressed. It is also conceivable, however, that such sub-cavities deliberately are not suppressed. For example, from a signal which not only goes back to the actual Fabry-Perot cavity 4, but also to the above-mentioned sub-cavities, the wavelength of the light coupled in might be inferred (e.g. from the course of a beat in the output signal of the filter).

It is of course also possible that the GRIN lenses are fixed in the cutout 14 in some other way, e.g. the fixation of the lenses 2, 3 each is not effected via their sides 22, 32, but via portions of their cladding region.

In addition, it is also conceivable in principle that the filter according to the invention is realized without the lenses 2, 3. In this case, the side walls 141, 142 of the cutout form the first and the second reflective structure of the Fabry-Perot cavity 4 and correspondingly can be provided with a reflection-increasing coating.

Via the distance L of the surfaces 21, 31, i.e. via the distance of the GRIN lenses 2, 3 from each other and thus via the length of the cutout 14, the free spectral range of the resonator formed by the Fabry-Perot cavity 4 is defined. The surfaces 21, 31 furthermore each in particular are provided with a reflection-increasing (e.g. dielectric) coating 211, 311. For example, at least one of the coatings is a highly reflective coating, for instance with a reflectivity in the range between 20% and 95%, in particular between 40% and 95%, e.g. at least 40%. It is conceivable that the coatings 211, 311 have identical or at least similar reflection properties. It is also possible, however, that the reflectivity of the coatings 211, 311 is different. In particular, the reflectivity of the coating 311 of the output lens 3 is smaller than that of the coating 311 of the input lens 2.

Figure 2A:
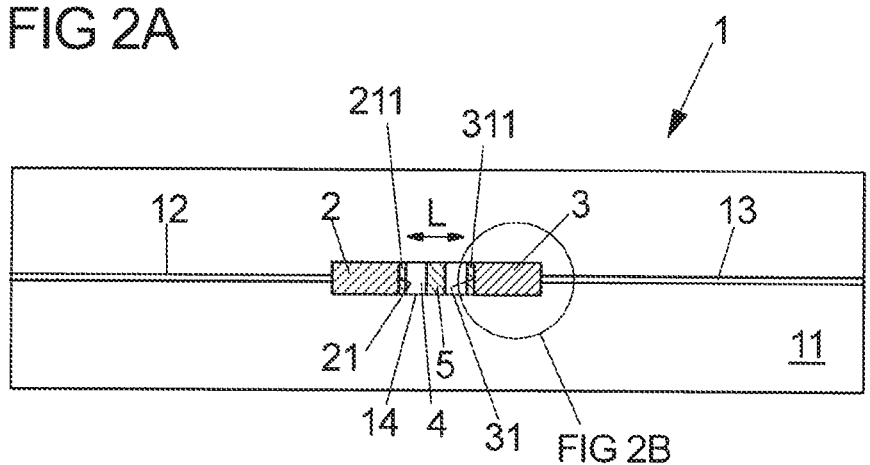
FIG. 2A shows a top view of the filter of FIG. 1.
Figure 2B:
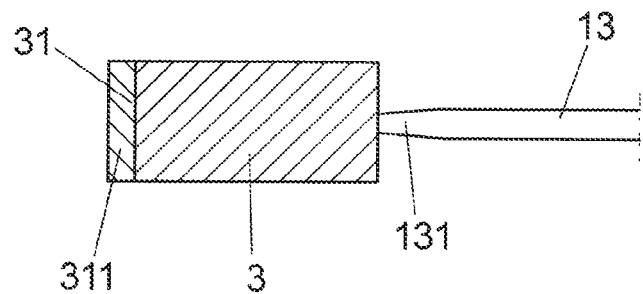
FIG. 2B shows a detail of FIG. 2A.

FIG. 2B shows a detail of the output side of the filter 1. Accordingly, the output lens 3 is connected with the output waveguide 13 via a taper 131. The taper 131 is a waveguide portion (in particular integrally connected with the waveguide 13) which flares from the lens 3 up to the waveguide 13 (it also is conceivable that the taper 131 flares towards the Fabry-Perot cavity 4, i.e. towards the waveguide 13, as already mentioned above). It is the purpose of the taper 131 to transform the modes of the light exiting from the lens 3 into modes guided through the waveguide 13. It is possible in addition that an analogous taper (not shown) also is used on the input side, i.e. there is a taper which connects the input waveguide 12 with the input lens 2.

Figure 3:
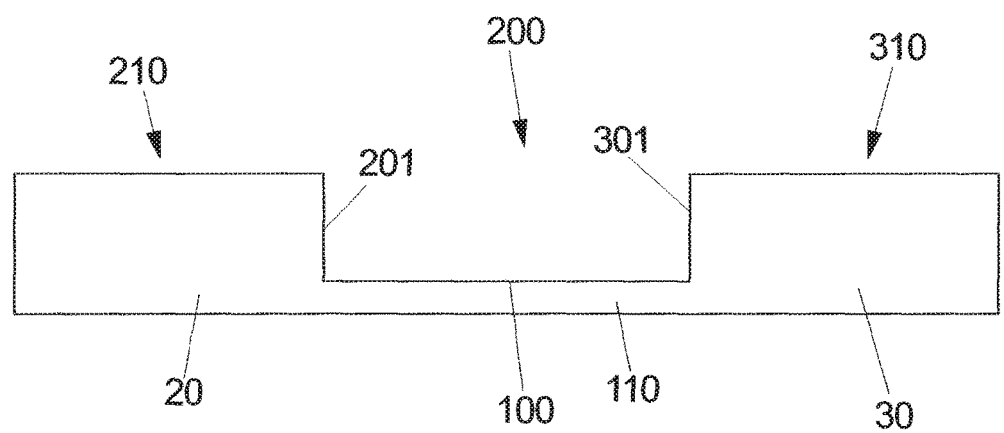
FIG. 3 shows a side view of a lens body for a filter according to another exemplary embodiment of the invention.

FIG. 3 schematically shows a side view of a (in particular cylindrical or cuboid) lens body 200 which serves to form a filter according to a further exemplary embodiment of the invention. With a first (in particular cylindrical) lens portion 20 the lens body 200 forms a first lens 210 which by a recess 100 is separated from a second lens 310 which is formed by a second (in particular likewise cylindrical) lens portion 30 of the lens body 200. The first lens portion 20 is integrally connected with the second lens portion 30 by a web 110. The lenses 210, 310 formed by the lens portions 20, 30 each are a GRIN lens.

The lens body 200 for example can be inserted into the cutout 14 of the substrate 11 instead of the separate lenses 2, 3 of the filter shown in FIG. 1. Thus, a surface 201 of the first lens portion 20 facing the recess 100 represents the first reflective structure of the filter and a surface 301 of the second lens portion 30 likewise facing the recess 100 forms the second reflective structure. Correspondingly, the surfaces 201, 301 can be provided with a reflection-increasing coating. It is also conceivable, however, that the lens body 200 is not inserted into a cutout of the substrate, but for example arranged on the substrate.

LIST OF REFERENCE NUMERALS 1 optical filter
2, 3, 210, 310 GRIN lens
4 Fabry-Perot cavity
11 substrate
12 input waveguide
13 output waveguide
14 cutout
20 first lens portion
21, 31 surface
22, 32 side
30 second lens portion
100 recess
110 web
131 taper
141, 142 side wall
200 lens body
201, 301 surface
211, 311 coating

The invention claimed is:

1. An optical filter, comprising
a substrate;
a first and a second reflective structure, which are spaced apart from each other such that they form a Fabry-Perot cavity; and
at least one optical waveguide formed on the substrate, via which light can be coupled into the Fabry-Perot cavity and/or out of the Fabry-Perot cavity,
wherein the Fabry-Perot cavity formed by the first and the second reflective structure at least partly is a free-beam cavity, wherein the waveguide is an integrated waveguide which is formed by one or more layers arranged on the substrate, and wherein the first and the second reflective structure are at least partly arranged in a cutout of the substrate or adjoin the cutout, and
wherein the first and/or the second reflective structure is formed by a surface of a GRIN lens arranged in the cutout.

2. The filter according to claim 1, wherein the first and/or the second reflective structure each include a reflection coating.

3. The filter according to claim 1, wherein the first and/or the second reflective structure each are formed by a side wall defining the cutout.

4. The filter according to claim 1, wherein the GRIN lens is formed such that it parallelizes incoming light.

5. The filter according to claim 1, wherein the first reflective structure is formed by a surface of a first lens portion of a lens body of the GRIN lens and the second reflective structure is formed by a surface of a second lens portion of the lens body of the GRIN lens.

6. The filter according to claim 5, wherein the lens body is formed in one piece.

7. The filter according to claim 5, wherein the lens body is arranged in the cutout.

8. The filter according to claim 1, further comprising a taper via which light can be coupled into the Fabry-Perot cavity.

9. The filter according to claim 1, wherein the Fabry-Perot cavity is filled with air or in the Fabry-Perot cavity a substance different from air is arranged for adjusting the properties of the filter.

10. The filter according to claim 1, further comprising a heating device for tempering at least a portion of the Fabry-Perot cavity.

11. An optical device comprising
a substrate; and
at least one optical waveguide formed on or in the substrate,
wherein the substrate includes a cutout, wherein via the optical waveguide light can be coupled into the cutout and/or out of the cutout, wherein the cutout is formed such that the light at least partly can propagate in the cutout as free beam,
wherein in the cutout at least one light-influencing device is arranged such that light can be coupled into the light-influencing device as free beam and/or light can be coupled out of the light-influencing device as free beam,
wherein the waveguide is an integrated waveguide which is formed by one or more layers arranged on the substrate, wherein a first and a second reflective structure are at least partly arranged in a cutout of the substrate or adjoin the cutout, and
wherein the first and/or the second reflective structure is formed by a surface of a GRIN lens arranged in the cutout.

12. The optical device according to claim 11, wherein the light-influencing device comprises an optical isolator, an optical circulator, a phase shifter and/or an optical amplifier.

13. The optical device according to claim 11, wherein in the cutout a Fabry-Perot cavity is formed or the cutout forms a Fabry-Perot cavity.

14. The optical device of claim 11, wherein the optical device is an optical filter.

15. A method for determining a property of a substance by using an optical filter which includes:
a substrate;
a first and a second reflective structure arranged in a cutout of the substrate, wherein the first and/or the second reflective structure is formed by a surface of a GRIN lens arranged in the cutout, and which are spaced apart from each other such that they form a Fabry-Perot cavity at least partly formed as free-beam cavity; and
at least one optical waveguide formed on the substrate, via which light can be coupled into the Fabry-Perot cavity and/or out of the Fabry-Perot cavity, wherein the waveguide is an integrated waveguide which is formed by one or more layers arranged on the substrate,
and the method comprising the following steps:
filling of the Fabry-Perot cavity of the filter with the substance;
coupling of light into the Fabry-Perot cavity;
receiving of light coupled out of the Fabry-Perot cavity; and
determining at least one property of the substance with reference to a spectrum of the light coupled out.

16. The method according to claim 15, wherein the substance is a liquid or a gas.

17. The method according to claim 15, wherein the Fabry-Perot cavity formed by the first and second reflective structure at least partly is a free-beam cavity.

* * * * *